US 6,587,730 B2

(12) United States Patent
Bernabei

(10) Patent No.: US 6,587,730 B2
(45) Date of Patent: Jul. 1, 2003

(54) METHOD AND APPARATUS FOR SKIN BROWN SPOT REMOVAL AND COLLAGEN FORMATION

(75) Inventor: Gian Franco Bernabei, Florence (IT)

(73) Assignee: Mattioli Engineering Ltd. (GB)

( * ) Notice: Subject to any disclaimer, the term of this patent is extended or adjusted under 35 U.S.C. 154(b) by 0 days.

(21) Appl. No.: 09/822,271

(22) Filed: Apr. 2, 2001

(65) Prior Publication Data

US 2002/0002392 A1 Jan. 3, 2002

Related U.S. Application Data

(63) Continuation-in-part of application No. 09/361,407, filed on Jul. 27, 1999, now Pat. No. 6,269,271.

(51) Int. Cl.⁷ .............................. A61F 7/12; A61F 2/00
(52) U.S. Cl. ........................................ 607/99; 607/101
(58) Field of Search ........................... 607/98, 99, 101, 607/104, 108; 606/34, 36, 39–50

(56) References Cited

U.S. PATENT DOCUMENTS

| 5,746,746 | A | | 5/1998 | Garito et al. | |
|---|---|---|---|---|---|
| 5,868,744 | A | | 2/1999 | Willmen | |
| 5,919,219 | A | * | 7/1999 | Knowlton | 606/33 |
| 5,938,657 | A | | 8/1999 | Assa et al. | |
| 6,063,085 | A | | 5/2000 | Tay et al. | |
| 6,104,959 | A | | 8/2000 | Spertell | |
| 6,117,109 | A | * | 9/2000 | Eggers et al. | 604/114 |
| 6,139,545 | A | | 10/2000 | Utley et al. | |
| 6,216,704 | B1 | * | 4/2001 | Ingle et al. | 128/898 |
| 6,277,116 | B1 | * | 8/2001 | Utely et al. | 606/42 |
| 6,309,387 | B1 | * | 10/2001 | Eggers et al. | 128/898 |
| 6,322,549 | B1 | * | 11/2001 | Eggers et al. | 604/114 |
| 6,350,276 | B1 | * | 2/2002 | Knowlton | 607/101 |
| 6,413,255 | B1 | * | 7/2002 | Stern | 606/41 |
| 6,416,514 | B1 | * | 7/2002 | Ein-Gal | 623/1.15 |

OTHER PUBLICATIONS

Castillo, G. D., "Procedures Laser Skin Surgery", Cosmetic Plastic Surgery, Web article updated 10/98.

* cited by examiner

Primary Examiner—Roy D. Gibson
(74) Attorney, Agent, or Firm—Foley & Lardner

(57) ABSTRACT

Radio frequency current pulses are applied to the skin in a controlled manner in order to heat selected volumes of skin, thereby inducing the removal of unwanted pigments from the skin and also enhancement of collagen formation on the skin. A probe provides the radio frequency current pulses to the skin, where the probe includes first and second metallic stripes, and where the probe is connected to two coaxial cables that are respectively connected to the first and second metallic stripes. The two coaxial cables are connected to a balanced/unbalanced transformer, which in turn is connected to a radio frequency generator that provides radio frequency pulses.

8 Claims, 2 Drawing Sheets

METHOD AND APPARATUS FOR SKIN BROWN SPOT REMOVAL AND COLLAGEN FORMATION

RELATED APPLICATIONS

This application is a continuation-in-part of U.S. patent application Ser. No. 09/361,407, filed Jul. 27, 1999, now U.S. Pat. No. 6,269,271 which is entitled METHOD AND APPARATUS FOR SKIN BROWN SPOT REMOVAL.

FIELD OF THE INVENTION

The present invention relates to a method and apparatus for skin brown spot removal and collagen formation, by using radio frequency pulses applied to the skin of a patient by a probe.

BACKGROUND OF THE INVENTION

It is well known that due to the aging process, some unwanted brown spots appears in the skin of the hands and arms. The color of the spots is mainly caused by a production of melanin.

Several methods have been tested in order to reduce the appearance of such spots, with these methods including the application of a laser at various wavelengths.

Some results have been achieved, but no method is at the present time is particularly effective and also does not have unwanted side effects.

When laser light reaches the skin, its intensity decreases exponentially in the skin. This means that the thermal energy that is delivered is higher in the first layer of the skin, and decreases exponentially as it penetrates lower into the lower layers of the skin. Moreover, the first corneum stratus (an upper skin layer) has a higher absorption than other portions of the skin. Such an energy profile is not suitable for uniform heating of a volume of skin due to the fact that in the superficial layers the reached temperature is too high and in other layers the temperature is not enough in order to trigger the desired brown spot reduction process.

It is well known that an alternating voltage applied to a conductor generates a current on the external layer of the conductor, and the depth of current flow depends on the frequency and the resistance of the conductor (skin effect).

SUMMARY OF THE INVENTION

The present invention relates to an apparatus and a treatment method of heating a portion of skin using radio frequency current pulses.

The present invention relates to an apparatus and a treatment method for the removal of unwanted brown spots on the skin and regeneration of the collagen.

According to the present invention, a heating triggers the decomposition of the melanin and induces a mild thermal injury to the collagen at a lower energy level than what is used to remove brown spots from the skin.

The present invention uses a pulsed radio frequency generator connected to a special probe for the coupling to the skin, and a water based substance for the enhancement of the effects. Such a combination is able to generate a controlled heating of a selected portion of the skin of a depth of 800 microns so that is possible to reach a temperature of 80 degrees Celsius, which triggers the decoloration of the melanin in the brown spots. At a lower temperature, such as 70 degrees Celsius, the effect is the injury of the collagen, thus inducing its regeneration. At this lower temperature, the melanin is not affected.

The method includes:
1) The application of radio frequency pulses at a frequency of 27 MHz on the skin over an area equal or less than 1 square centimeter for a time of less than 0.5 second and a power of less than 100 W.
2) An apparatus which includes the following to perform the preceding treatment:
   a) A radio frequency generator functioning in pulsed mode with powers and wavelengths in the ranges previously specified;
   b) a probe for applying the radio frequency current which permits concentration of heating in the selected volume of the skin;
   c) an impedance transformer in order to adapt the high impedance of the skin to the low impedance of the radio frequency generator.
3) The application on the skin of a water-based gel in order to decrease the impedance of the first layer of the skin and at the same time carry during the treatment additional substance that are usually employed for decreasing the appearance of the brown spots, such as cogic acid.

BRIEF DESCRIPTION OF THE DRAWINGS

The invention will become more fully apparent from the following detailed description when read in conjunction with the accompanying drawings with like reference numerals indicating corresponding parts throughout, and wherein.

DETAILED DESCRIPTION OF THE PREFERRED EMBODIMENTS

According to the present invention, a water based gel is preferably applied to the skin area to be treated, prior to treatment. The effect of such a water based gel is to decrease the superficial electrical impedance to a value independent from the type and condition of the patient's skin.

Figure 2:
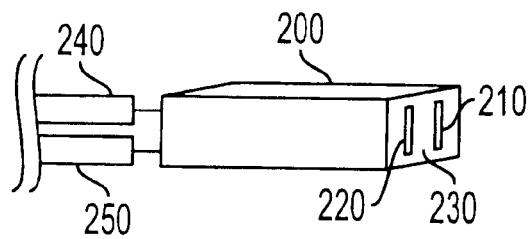
FIG. 2 is a plan view of a probe of the skin brown spot removal apparatus according to the invention.

A special probe that includes two electrodes is positioned on the gel that has been applied to the patient's skin. The probe has two metallic stripes, each having a dimension of 3 millimeter width×5 millimeter length and where the two metallic stripes are separated from each other by a distance of 5 millimeters, with an insulator such as plexiglass or plastic providing the separation. Other dimensions of the metallic stripes are possible while remaining within the scope of the invention, with those dimensions depending on the size of the brown spot to be removed. FIG. 2 shows a plan view of a probe 200 that includes a first metallic stripe 210, a second metallic stripe 220, and with insulator 230 provided between the first and second metallic stripes 210, 220. In the preferred embodiments, the entirety of the probe 200, except for the metallic stripes 210, 220 and any coaxial connection ports, is made of the insulator material.

Figure 3:
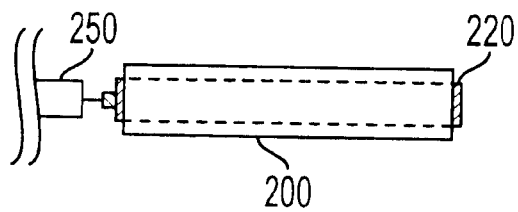
FIG. 3 is a side view of the probe according to the invention.
Figure 4:
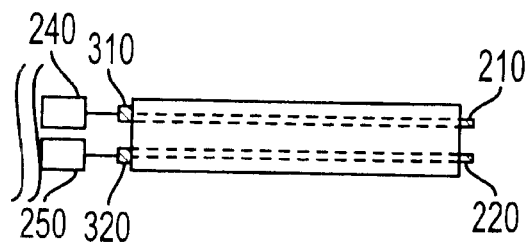
FIG. 4 is a top view of the probe according to the invention.

FIG. 3 shows a side view of the probe 200, in which a coaxial connection port 320 is provided on the probe 200 for connection to the coaxial cable 250. FIG. 4 shows an upper view of the probe 200, with both the coaxial connection port 320 and another coaxial connection port 310 of the probe 200 shown. The metallic stripes 210, 220 are mainly shown as dashed lines in FIG. 4 (except for the small portion extending out of the front side of the probe 200), since they are embedded within the probe 200.

As seen in FIGS. 2, 3 and 4, the two electrodes 210, 220 are respectively connected to two separate coaxial cables 240, 250 each having a length of 2.5 meters, and each acting as an impedance transformer. Of course, other cable lengths are possible while remaining within the scope of the invention. The cables 240, 250 are used in order to adapt the high impedance of the skin to the low impedance of the radio frequency generator that operates at a preferred frequency of 27 Mhz. The radio frequency generator may operate at other frequencies within the Mhz range while remaining within the scope of the invention.

Figure 1:
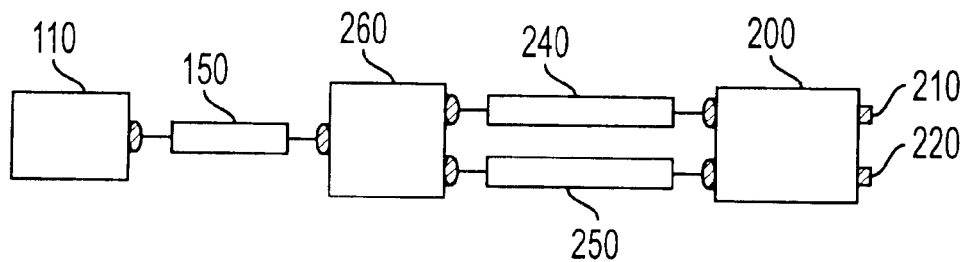
FIG. 1 is a block diagram of a skin brown spot removal apparatus according to the invention.

As shown in FIG. 1, the radio frequency generator 110 is connected to the two cables 240, 250 by way of a balanced-unbalanced transformer 260. The radio frequency generator 110 is preferably connected to the balanced-unbalanced transformer 260 by way of a coaxial cable 150.

The radio frequency generator 110 is capable of generating programmable pulses of selected time and peak power. Typical parameters are 100 millisecond time, 50 W peak power and 27 Mhz frequency. Other parameters are possible while remaining within the scope of the invention, with those parameters being selected based on the size of the probe and the desired penetration depth.

The radio frequency pulses generate an electromagnetic field between the two electrodes. The current density on the skin decrease sharply with the depth after 800 micron due to the skin effect. In such a way, the heating takes place only in a skin volume of about 5000×5000×800 microns. Moreover, the matching of the pulse duration with the thermal inertia of the skin and the thermal resistance enables the creation of an even (e.g., monotonic) increase of the temperature in the selected volume, thereby avoiding the problem of having the upper layers being too hot. The insulator between the two electrodes also has the function of keeping the first layer of the skin cool, thereby providing for a faster decrease of the skin temperature after a pulse has been applied (and before a next pulse is applied). The controlled heating of the area destroys the temperature-sensitive pigments without generating damage to the skin In a second embodiment, the effect is enhanced by the employment of substances that normally are used in order to decrease the appearance of the brown spot, such as cogic acid.

A third embodiment is described below, for inducing collagen formation in the skin. The third embodiment uses a lower energy than the first two embodiments described above. That lower energy corresponds to about 20% of the energy used in the first two embodiments. That is, instead of 50 W peak power at 100 millisecond, i.e. 5 joule, pulses having a 20 W peak power at 250 millisecond are provided to the skin surface, i.e. 4 joule. Besides the lower power output and different treatment time, and by using a lower frequency output, such as 14 MHz instead of 27 MHz, the equipment set up in the third embodiment is the same of the first and second embodiment.

Due to the lower-power pulses and the lower energy provided to the skin in the third embodiment, the skin temperature reached is lower, at or around 70 degrees Celsius. In the third embodiment, due to the lower skin temperature, no discoloration of melanin occurs. However, the elevated heat causes thermal injury, which generates some damage to the collagen in the skin. After the application of pulses in accordance with the third embodiment, the skin reacts to the pulses, thereby regenerating the collagen and thereby resulting in a smoothing of the wrinkles in the treated skin.

Other configurations of the equipment and treatment conditions in accordance with the third embodiment are possible. As an example, in order to treat a larger skin area at the same time, it is possible to increase the number of electrodes, and also to increase the applied power.

Figure 5A:
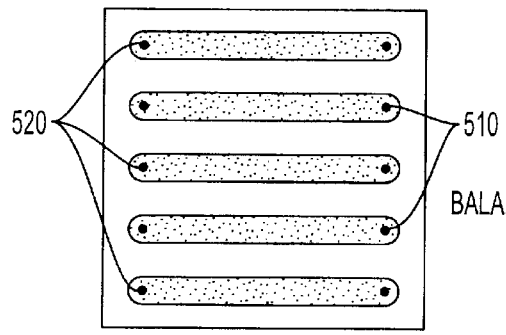
FIGS. 5A and 5B show a skin-side view and a back view, respectively, of an electrode structure according to one configuration of a third embodiment of the invention.
Figure 5B:
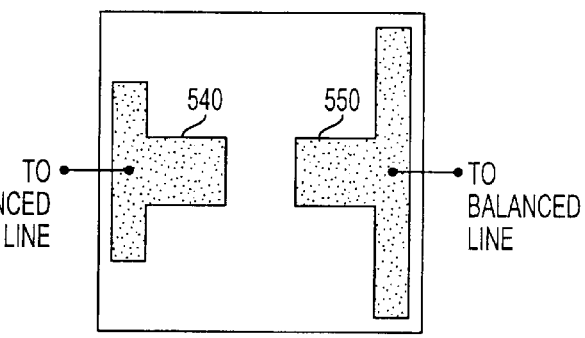

Several configuration of the electrodes are possible, but all remain within the scope of the present invention:

1. In order to treat a 1 square centimeter region, the electrodes required are at least three in number, and of a length of 10 mm each, and spaced apart from each other by 5 mm. The power needed is 4 times the power described above (20 W*4=80 W) due to the fact that the area treated is four times the area of the preferred embodiment. The electrodes that are not adjacent (first and third electrodes on the probe) are electrically connected to each other. FIGS. 5A and 5B show the connections of the even-spaced electrodes 510 to each other, as well as the connections of the odd-spaced electrodes 520 to each other, at the head of a probe. In this configuration, as little as three electrodes are required, but more may be used. FIG. 5A is a skin-side view of the electrodes, and FIG. 5B is a back-side view, showing the connections of various electrodes to each other. Connection 540 connects the even-spaced electrodes to each other, with the connection 540 providing an electrical connection to one of the two coaxial cables 240, 250 (via the first metallic stripe 210, as shown in FIG. 2). Connection 550 connects the odd-spaced electrodes to each other, with the connection 550 providing an electrical connection to the other of the two coaxial cables 240, 250 (via the second metallic stripe 220, as shown in FIG. 2).

2. In order to treat a 4 square centimeter skin region, the electrodes required are at least five in number, and of a length of 20 mm each, and spaced apart from each other by 5 mm. The power needed is four times the power of the previous configuration (80 W*4=320 W). The electrodes that are not adjacent to each other on the probe are electrically connected to each other. Again, the alternate-electrode connection as shown in FIGS. 5A and 5B may be used.

Figure 6A:
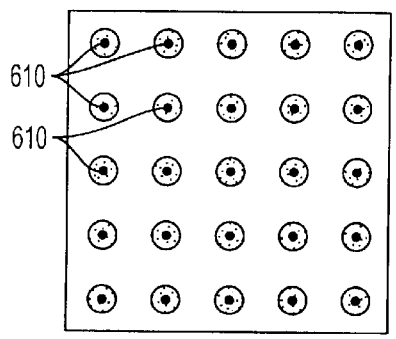
FIGS. 6A and 6B show a skin-side view and a back view, respectively, of an electrode structure according to another configuration of the third embodiment of the invention.
Figure 6B:
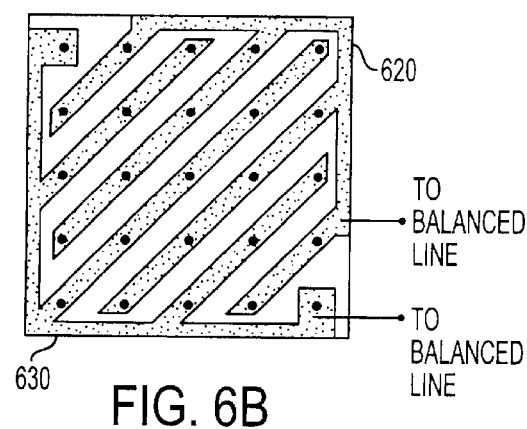

3. A further configuration of electrodes for treating a large skin area at the same time, such as 4 square centimeter area, is with 25 round electrodes each having a diameter of 2 mm. The power is the same as the previous configuration (320 W). The electrodes not adjacent to each other on the probe are electrically connected to each other. FIG. 6A shows a skin-side view of 25 round electrodes 610 provided at the head of a probe. FIG. 6B shows a back-side view, in which the electrical connection of the electrodes can be seen. Electrical connection 620 connects a first set of the electrodes 610 to each other, and electrical connection 630 connects a second set of the electrodes to each other. Electrical connection 620 provides a connection to one of the two coaxial cables 240, 250 (via the first metallic strip 210, as shown in FIG. 2), and electrical connection 630 provides a connection to the other of the two coaxial cables 240, 250 (via the second metallic stripe, as shown in FIG. 2).

In order obtain a better uniformity of the density of power applied on the skin, but which results in a somewhat increased complexity of the third configuration of the system according to the third embodiment, it is possible to have the electrodes spaced apart by 2.5 mm instead of 5 mm. In such a configuration, each metallic stripe the probe has a width of 1 mm. In this closely-packed electrode configuration, each of the round electrodes has a diameter of 1 mm.

While preferred embodiments have been described herein, modification of the described embodiments may become apparent to those of ordinary skill in the art, following the teachings of the invention, without departing from the spirit and scope of the invention as set forth in the appended claims.

I claim:

1. A treatment system for enhancing collagen production on a region of a patient's skin, comprising:
    an applying unit that includes a water based collagen for applying the water based collagen to patient's skin, the water based collagen including cogic acid in order to remove any brown spots from the patient's skin;
    a pulsed radio frequency generator with an operating power of between 1 and 100 W, and with an operating frequency of between 7 MHz and 52 MHz, and with an output pulsewidth of between 1 and 500 millisecond; and
    a probe that is connected to the pulsed radio frequency generator, the probe including at least three electrodes,
    wherein the at least three electrodes of the probe are directly applied to the skin in order to enhance collagen formation on the region of the patient's skin.

2. A treatment system as in claim 1, wherein the probe is applied to the region of the patient's skin of less than one square centimeter in size.

3. A treatment system as in claim 1, wherein the energy output by the pulsed radio frequency generator is no greater than 4 joule on an area of 0.25 square centimeter, in order to limit thermal damage to the collagen, thus enabling regeneration of the collagen and wrinkle reduction on the region of the patient's skin.

4. A treatment system as in claim 1, wherein the probe has at least four electrodes for treatment of a skin region greater than 2 square centimeters.

5. A treatment system as in claim 1, wherein none of the at least three electrodes are return electrodes.

6. A method for enhancing collagen formation on a region of a patient's skin, comprising:
    applying at least one pulse from an radio frequency generator that operates at between 1 and 100 W, a frequency of between 7 and 52 MHz, and a pulsewidth of between 1 and 500 milliseconds; and
    providing the at least one pulse to the skin of the patient by way of a probe connected to the radio frequency generator,
    wherein the probe has at least five electrodes for treatment of a skin region greater than 2 square centimeters,
    wherein the at least five electrodes are round electrodes that are disposed in a matrix of electrodes having a plurality of columns and a plurality of rows,
    wherein, in the providing step, the at least one pulse is provided to the skin of the patient at a first instant in time by way of a first subset of electrodes that are electrically coupled to each other and that are positioned on non-adjacent diagonal lines in the matrix of electrodes.

7. A method as in claim 5, further comprising:
    before the applying step, providing a water based conductive substance on the region of the patient's skin where the probe is to be applied thereto.

8. A treatment system for enhancing collagen production on a region of a patient's skin, comprising:
    a radio frequency generator that outputs at least one pulse at a power of between 1 and 100 W, at a frequency of between 7 and 52 MHz, and at a pulsewidth of between 1 and 500 milliseconds; and
    a probe that is connected to the radio frequency generator and that provides the at least one pulse to the skin of the patient,
    wherein the probe includes at least three electrodes that are in direct contact with the region of the patient's skin when the at least one pulse is provided to the region of the patient's skin,
    wherein the at least three electrodes include at least five electrodes that are round electrodes and that are disposed in a matrix of electrodes having a plurality of columns and a plurality of rows, and
    wherein the at least one pulse is provided on to the region of the patient's skin at a first instant in time by way of a first subset of electrodes that are electrically connected to each other and that are positioned on non-adjacent diagonal lines in the matrix of electrodes.

* * * * *